United States Patent [19]
Thomsen

[11] Patent Number: 6,015,545
[45] Date of Patent: *Jan. 18, 2000

[54] MANGANESE CONTAINING MAGNETIC RESONANCE CONTRAST AGENT

[76] Inventor: Henrik S. Thomsen, Ved Orehoj 6, DK-2900 Hellerup, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/677,051

[22] Filed: Jul. 9, 1996

[30] Foreign Application Priority Data

Jul. 11, 1995 [DK] Denmark ................................. 0810/95

[51] Int. Cl.$^7$ ................................................... A61K 5/055
[52] U.S. Cl. ..................... 424/9.36; 424/639; 514/492; 514/836; 426/73; 426/74; 600/420
[58] Field of Search ................................ 424/9.36, 639; 514/492, 836; 436/173; 128/653.4, 654; 426/73, 74; 600/420

[56] References Cited

U.S. PATENT DOCUMENTS

| | | |
|---|---|---|
| 4,863,898 | 9/1989 | Ashmead et al. ............................ 514/6 |
| 4,985,233 | 1/1991 | Klaveness et al. .......................... 424/9 |
| 4,994,442 | 2/1991 | Gil et al. .................................... 514/45 |
| 5,064,636 | 11/1991 | Li et al. ...................................... 424/9 |
| 5,122,363 | 6/1992 | Balkus, Jr. et al. ......................... 424/9 |
| 5,128,121 | 7/1992 | Berg et al. .................................. 424/9 |
| 5,215,750 | 6/1993 | Keane, II .................................. 424/440 |
| 5,340,603 | 8/1994 | Neylan et al. ............................. 426/73 |
| 5,422,127 | 6/1995 | Dube et al. ................................ 426/73 |
| 5,534,240 | 7/1996 | Hasegawa et al. ..................... 424/9.36 |

FOREIGN PATENT DOCUMENTS

| | | |
|---|---|---|
| A2 308983 | 3/1989 | European Pat. Off. . |
| WO 96/05867 | 2/1996 | WIPO . |

*Primary Examiner*—Gary E. Hollinden
*Attorney, Agent, or Firm*—Merchant & Gould P.C.

[57] ABSTRACT

A composition for use as a contrast medium being particularly suitable for imaging of the stomach, liver, bile duct and gall bladder, said composition comprising as an active ingredient a physiologically acceptable manganese compound and an uptake promoter, wherein the uptake promoter comprises a physiologically acceptable reducing compound containing a physiologically acceptable amino acid or a salt thereof, and/or vitamin D.

20 Claims, 3 Drawing Sheets

MANGANESE CONTAINING MAGNETIC RESONANCE CONTRAST AGENT

The present invention relates to improvements on and relating to magnetic resonance imaging (MRI) and in particular to compositions for use as or in the preparation of MRI contrast media for imaging of the stomach, liver, bile duct and gall bladder. The MRI contrast media may also be used for imaging the pancreas and the heart.

MRI is now well established as a medical diagnostic tool. The ability of the technique to generate high quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging nuclei"—generally water protons in body fluids and tissues) responsible for the magnetic resonance (MR) signals from which the images are generated may be used to enhance image contrast and, accordingly, in recent years, many such materials have been suggested as MRI contrast agents.

The enhanced contrast obtained with the use of contrast agents enables particular organs or tissues to be visualised more clearly by increasing or by decreasing the signal level of the particular organ or tissue relative to that of its surroundings, Contrast agents raising the signal level of the target site relative to that of its surroundings are termed "positive" contrast agents whilst those lowering the signal level relative to surroundings are termed "negative" contrast agents.

The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration parameter known as arising from the effect on the imaging nuclei of the fields generated by the ferromagnetic or superparamagnetic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substances at the imaged site, the nature of the paramagnetic substance itself, and the pulse sequence and magnetic field strength used in the imaging routine.

Generally, however, paramagnetic contrast agents are positive MRI contrast agents at low concentrations where their $T_1$ lowering effect dominates, and negative MRI contrast agents at higher concentrations where their $T_2$ lowering effect is dominant. In either event, the relaxation time reduction results from the effect on the imaging nuclei of the magnetic fields generated by the paramagnetic centres.

The use of paramagnetic, ferromagnetic and superparamagnetic materials as MRI contrast agents has been widely advocated, and broad ranges of suitable materials have been suggested in the literature.

An example of a physiologically acceptable paramagnetic material known for use as an MRI contrast agent is manganese ion, which may conveniently be used in the form of its salts, chelates or other complexes. Indeed, even at very low intravenuos dosages (about 5–10 $\mu$mol/kg body weight) manganese ions have been found to be particularly effective as a contrast agent for imaging of the liver.

However, manganese, when administered intravenously as a contrast agent, may be teratogenic at clinical dosages. Administered intravenously, manganese is also known to interfere with the normal functioning of the heart by replacement of calcium in the calcium pump of the heart. It has been reported that dosages of manganese injected into rats in excess of 0.1 mmol/kg body weight were often lethal.

In order to reduce the direct effect on the heart, oral administration has been proposed, This ensures passage of the contrast agent through the liver before going to the heart and thereby decreasing the possibility of a heart attack.

Oral administration of $MnCl_2$ as a liver imaging MR contrast agent has been proposed, and orally administered $MnCl_2$ has not been found to be teratogenic. However, the adsorption of $MnCl_2$ through the gut is poor, and as a result the dosage required for clinical efficacy is of the order 100–1000 $\mu$mol/kg body weight. In the event of damage to the gut resulting in increased uptake, such a high dosage level still has the potential for causing undesired adverse effects, e.g. cardiac effects.

The toxicity of manganese ions precludes their administration in amounts large enough to be useful in MRI. It has been found that paramagnetic chelates are less toxic than the free ions, but the chelation will prevent or reduce the enhancement of binding of paramagnetics with tissues. This means that a greater amount of the chelate will be needed to produce the same effect as the free ions.

EP A2 308 983 describes a MR imaging composition containing manganese(II) coordination compounds and their use in MRI. The invention is in particular directed to manganese(II) coordination complexes with water-soluble amino acids, to MR imaging compositions containing these complexes, and to their use in MRI. These compounds have proven to be more safe and provide the same relaxivity as manganese salts. The non-chelated compounds do not affect the binding of manganese to body tissue and blood components, and particularly heart and liver tissue, and reduce the toxicity. Solutions of the compound can be administered rectally, orally or parenterally, preferably parenterally.

Although it is stated that these solutions may be administered orally, none of the examples show what oral dosage is neccessary to achieve a measuarable MR image. Only injected dosages have been reported, and these dosages are not suffient for oral administration.

We have now surprisingly found that gastrointestinal tract manganese contrast agents suitable for imaging of the liver may be produced by the incorporation of an uptake promoter capable of enhancing manganese transport across the membranes of the gastrointestinal tract.

Compounds which have been found to be suitable for use as uptake promoters include amino acids, vitamin D or a combination thereof.

Thus, viewed from one aspect the present invention provides a contrast medium composition comprising a physiologically acceptable manganese compound, an uptake promoter and a physiologically acceptable carrier or excipient, wherein the uptake promoter comprises an amino acid and/or vitamin D.

The contrast medium composition according to the invention may comprise a manganese compound together with a mixture of several uptake promoters, i.e. a mixture of several amino acids and/or vitamin D.

The manganese compound, which preferably is soluble in gastrointestinal fluid, may for example be a salt, a chelate or another complex, or may be a mixture of different salts, chelates and/or complexes. Particularly preferred are metal chelates and salts in which the manganese is present as Mn(II) rather than Mn(III), since the former has a higher magnetic moment and thus is more effective as a MR contrast agent. Suitable salts are salts of inorganic anions, e.g. chlorides, bromides, iodies, flourides, sulfates, phosphates, preferably chlorides and salts of organic anions.

Another manganese source is manganese containing foodstuff such as blueberry juice, green tea and nuts. Also these manganese sources may be combined with an uptake promoter according to the invention.

The reducing nature of the uptake promoter is important since normal uptake of manganese by the gut tends to favour Mn(II) rather than Mn(III).

Examples of amino acids which have been found to be effective as uptake promoters in the compositions of the invention include all the native amino acids, i.e. alanine, valine, leucine, tryptophan, methionine, isoleucine, proline, phenylalanine, serine, glycine, threonine, cysteine, aspargine, glutamine, tyrosine, aspartic acid, glutamic acid, arginine, lycine and histidine. Particularly preferred as an uptake promoter in the composition of the invention are the amino acids L-aspartic acid and L-alanine.

The preferred vitamin is vitamin $D_3$, but all subgroups of vitamin D are suitable. Vitamin D is a fat soluble vitamin and soluble in organic solvents. A preferred solvent is polyethylene glycol.

The increase in the uptake of manganese for various uptake promoters is demonstrated in the figures, which are MR images of the liver of rats after administering the contrast medium composition orally.

Using the compositions of the invention, the liver can be effectively MR imaged with a significant reduction in the dosage of manganese otherwise required when administered orally.

BRIEF DESCRIPTION OF THE DRAWINGS

The figures illustrate cross section images of the body of rats in the liver region. The groups are defined in the example.

The signal intensities were as follows:
    Group 2: Average signal intensity 112
    Group 5: Average signal intensity 134
    Group 1: Average signal intensity 98
    Group 7: Average signal intensity 121

Figure 2:
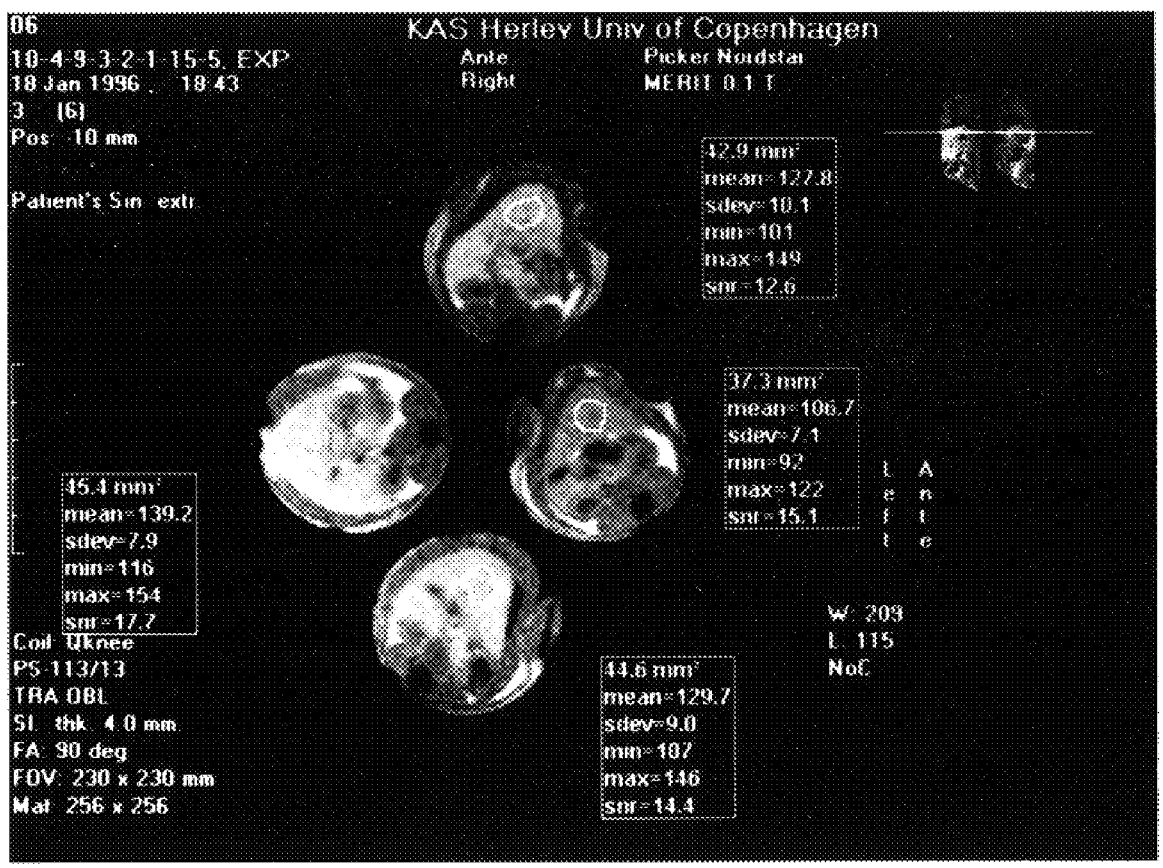

FIG. 2 illustrates images from rats of group 4 (top), group 3 (mid left), group 1 (control) (mid right), and group 7 (bottom).

The signal intensities were as follows:
    Group 4: Average signal intensity 127
    Group 3: Average signal intensity 139
    Group 1: Average signal intensity 106
    Group 7: Average signal intensity 129

Figure 3:
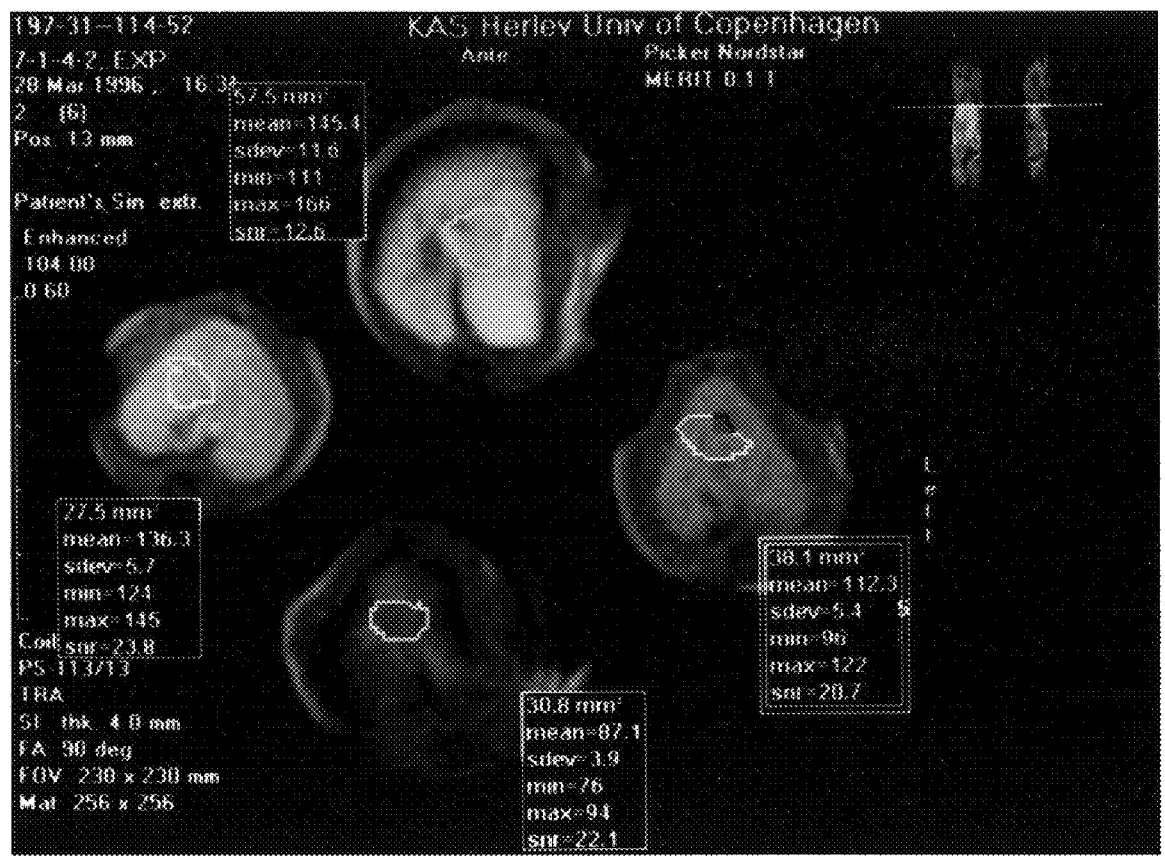

FIG. 3 illustrates images from rats of group 7 (top), group 4 (mid left), group 1 (control) (mid right), and group 2 (bottom).

The signal intensities were as follows:
    Group 7: Average signal intensity 146
    Group 4; Average signal intensity 135
    Group 1: Average signal intensity 109
    Group 2: Average signal intensity 101

DETAILED DESCRIPTION OF THE INVENTION

In the composition according to the invention, the preferred molar ratio of manganese to uptake promoter is from 1:0.2 to 1:50, preferably 1:1 to 1:20, more preferably 1:3 to 1:6, and most preferably about 1:5.

If desired, the uptake promoter may be present in whole or in part as the counterion to the manganese ions.

The composition according to the invention may be used to achieve a so-called "double contrast effect" by increasing the signal level from the liver whilst at the same time decreasing that from the surrounding tissues, in particular from the gut. Such an effect enables yet further enhancement of the image of the liver.

In a particularly preferred embodiment, the composition of the invention may be used in combination with a second contrast agent having either a positive or negative contrast effect. Preferably, the compositions of the invention are used in combination with a second contrast agent having an opposing contrast effect. This results in a "double contrast effect" enabling visualisation and margin definition of the liver to be particularly enhanced.

As mentioned above, paramagnetic materials, such as manganese ions, may act as either positive or negative MRI contrast agents depending upon a number of factors, including the concentration of the ions at the imaging site and the magnetic field strength used in the imaging procedure. At the concentrations of manganese comtemplated for use in the compositions of the invention, the manganese-containing contrast agent will in general function as a positive contrast agent. The second contrast agent is therefore conveniently negative contrast agent and may be any negative MRI contrast agent suitable for oral administration.

Examples of contrast agents for use in combination with the composition of the invention include iron (Fe), gadolinium (Gd) and dyprosium (Dy).

When using the composition of the invention to achieve a double contrast effect, it is particularly preferable to incorporate a viscosity enhancing agent which attains its full viscosity enhancing effect only after administration of the contrast medium. The contrast medium is thus able to be ingested in a relatively tolerable form while yet developing the desired viscosity at or during passage towards the site which is to be imaged.

The compositions of the invention are particularly suited to use, if required, after dispersion in aqueous media, for imaging of the liver. For such a purpose the composition may be administered into the gastrointestinal tract orally, rectally or via a stomach tube.

Thus, viewed from a further aspect the present invention provides a method of generating a magnetic resonance image of a human or non-human, preferably mammalian, animal body, which method comprises administering into the gastrointestinal tract of said body an effective amount of a contrast medium comprising a physiologically acceptable manganese compound and a physiologically acceptable reducing compound containing a physiologically acceptable amino acid or a salt thereof, and/or vitamin D, and generating a magnetic resonance image of the liver and the gastrointestinal tract of said body, In a further embodiment the invention provides a method of generating a magnetic resonance image of a human or non-human animal body, which method comprises administering into the gastrointestinal tract of said body an effective amount af a composition comprising: (a) a first contrast agent comprising a physiologically acceptable manganese compound and a physiologically acceptable reducing compound containing a physiologically acceptable amino acid or a salt thereof, and/or vitamin D, together with (b) a second contrast agent and generating a magnetic resonance image of the liver and abdomen of said body.

It is possible to formulate the contrast medium immediately or shortly prior to administration by mixing the uptake promoter with the manganese species, Thus, in a further aspect the invention also provides a MRI contrast agent kit comprising in a first container a physiologically acceptable manganese compound, and in a second container a physiologically acceptable reducing compound containing an amino acid or a salt thereof, and/or vitamin D.

In a further embodiment of the invention the first container comprises a first contrast agent comprising a physiologically acceptable manganese compound together with a physiologically acceptable reducing compound containing an amino acid or a salt thereof, and/or vitamin D, and the second container comprises a second contrast agent.

The contrast agent composition of the invention may of course include components other than the uptake promoter, the manganese compound, for example conventional pharmaceutical formulation aids, such as wetting agents, buffers, disintegrants, binders, fillers, flavouring agents and liquid carrier media, such as sterile water, water/ethanol etc.

For oral administration, the pH of the composition is preferably in the acid range, e.g. 2 to 7, and while the uptake promoter may itself serve to yield a composition with this pH, buffers or pH adjusting agents may be used.

The contrast media may be formulated in conventional pharmaceutical administration forms, such as tablets, capsules, powders, solutions, dispersions, syrups, suppositories etc. When the contrast media can be administered orally, a patient can administer the contrast media himself 2 to 3 hours before being scanned. The patient is not obliged to stay in the hospital for several hours before being scanned.

The preferred dosage of the composition according to the present invention will vary according to a number of factors, such as the administration route, the age, weight and species of the subject, and the particular uptake promoter used. Conveniently, the dosage of manganese will be in the range from 5 to 500 $\mu$mol/kg body weight, preferably from 5 to 150 $\mu$mol/kg body weight, more preferably from 10 to 100 $\mu$mol/kg body weight, while the dosage of the uptake promoter will be in the range from 5 $\mu$mol to 1 mmol/kg body weight, preferably from 25 $\mu$mol to 0.5 mmol/kg body weight.

The following example illustrates the effectiveness of the uptake of manganese for various uptake promoters.

The studies were carried out on seven groups of rats with six rats in each group. MRI examination was done with a quadrature knee-coil in a 0.1 T MRI unit. Each scanning included four rats, and the examination was carried out three hours after the contrast medium was administered to the rats. If experiments are carried out with a higher tesla unit, e.g. 1.0 or 1.5 T, a larger increase in signal intensity can be expected.

After a 12 hour diet various contrast medium compositions were orally administered to the various groups of rats. The contrast medium was administered to the stomach of the rats via a catheter. Three hours after administration the rats were killed and placed in a tube. Thereafter the rats were scanned.

The following non-limiting example illustrates various compositions administered to various groups of rats. The results of the scannings are illustrated in the figures.

In the example the units $\mu$mol/kg and mg/kg refer to $\mu$mol/kg body weight and mg/kg body weight

EXAMPLE A

To group 1 (control) no contrast medium was administered.

To group 2 100 $\mu$mol/kg (19.6 mg/kg) manganese(II) chloride tetrahydrate were administered.

To group 3 100 $\mu$mol/kg (19.8 mg/kg) manganese(II) chloride tetrahydrate and 300 $\mu$mol/kg (42 mg/kg) L-aspartic acid were administered.

To group 4 100 $\mu$mol/kg (19.8 mg/kg) manganese(II) chloride tetrahydrate, 300 $\mu$mol/kg (42 mg/kg) L-aspartic acid and 0.1 mg/kg vitamin $D_3$(10 $\mu$g/ml) were administered.

To group 5 100 $\mu$mol/kg (19.8 mg/kg) manganese(II) chloride tetrahydrate and 300 $\mu$mol/kg (25 mg/kg) L-alanine were administered.

To group 6 100 $\mu$mol/kg (19.8 mg/kg) manganese(II) chloride tetrahydrate, 300 $\mu$mol/kg (25 mg/kg) L-alanine and 0.1 mg/kg vitamin $D_3$(10 $\mu$g/ml) were administered.

To group 7 100 $\mu$mol/kg (19.8 mg/kg) and 0.1 mg/kg vitamin $D_3$ (10 $\mu$g/ml) were administered.

Figure 1:
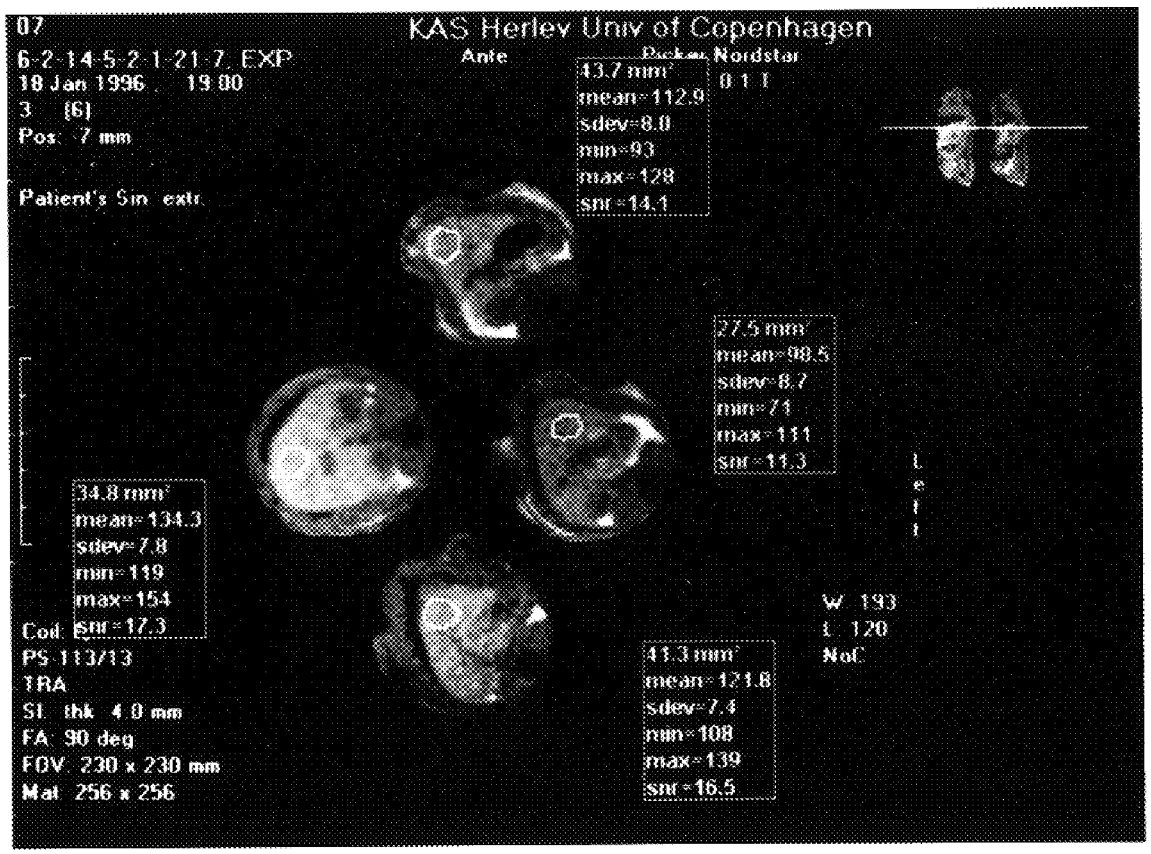
FIG. 1 illustrates images from rats of group 2 (top), group 5 (mid left), group 1 (control) (mid right), and group 7 (bottom).

Now referring to FIG. 1 it can be seen that the average signal intensity of the liver is substantially increased after administration orally of manganese(II)chloride tetrahydrate and L-alanine or manganese(II)chloride tetrahydrate and vitamin $D_3$, respectively.

Referring to FIG. 2 it can be seen that the average signal intensity of the liver is substantially increased after administration orally of manganese(II)chloride tetrahydrate and L-aspartic acid and vitamin $D_3$, L-aspartic acid or vitamin $D_3$, respectively.

Referring to FIG. 3 it can be seen that the average signal intensity of the liver is substantially increased after administration of manganese(II)chloride tetrahydrate and vitamin D3 or manganese(II)chloride tetrahydrate and L-aspartic acid and vitamin $D_3$, respectively.

The following example illustrates preferred compositions administered to a human depending on the body weight.

EXAMPLE B

TABLE

| Body weight (kg) | Manganese (II) chloride tetrahydrate (g) | L-alanine (g) |
| --- | --- | --- |
| 60 | 1,188 | 1,500 |
| 70 | 1,386 | 1,750 |
| 80 | 1,568 | 2,000 |
| 90 | 1,782 | 2,250 |
| 100 | 1,980 | 2,500 |

Before being administered to the human the manganese (II) chloride tetrahydrate and L-alanine are dissolved in 250 ml of water.

I claim:

1. A contrast medium composition consisting essentially of a physiologically acceptable manganese compound, a vitamin D, and a physiologically acceptable amino acid or a salt thereof; the contrast medium producing contrast for magnetic resonance imaging upon administration to a patient in need of magnetic resonance imaging.

2. A composition as claimed in claim 1, wherein the manganese compound is a salt, a chelate or another complex in which the manganese is present as Mn(II).

3. A composition as claimed in claim 1 wherein the amino acid is an $\alpha$- or $\beta$-amino acid.

4. A composition as claimed in claim 3, wherein the amino acid is alanine, valine, leucine, tryptophan, methionine, isoleucine, proline, phenylalanine, serine, glycine, threonine, cysteine, asparagine, glutamine, tyrosine, aspartic acid, glutamic acid, arginine, lysine, or histidine.

5. A composition as claimed in claim 1, wherein the amino acid, vitamin D, or both are present in whole or in part as the counterion to the manganese ion.

6. A composition as claimed in claim 1 further consisting essentially of a physiologically acceptable carrier or excipient.

7. A contrast medium composition according to claim 1, further consisting essentially of blueberry juice, green tea, or nuts.

8. A composition as claimed in claim 1, wherein the vitamin is Vitamin $D_3$.

9. A composition as claimed in claim 4, wherein the amino acid is L-alanine or L-aspartic acid.

10. A MRI contrast agent kit consisting essentially of in a first container a physiologically acceptable manganese compound, and in a second container a physiologically acceptable amino acid or a salt thereof and vitamin D.

11. A method of generating a magnetic resonance image of a human or non-human animal body, which method comprises:

administering into the gastrointestinal tract of the body of a subject in need of magnetic resonance imaging a contrast medium consisting essentially of a physiologically acceptable manganese compound, a vitamin D, and a physiologically acceptable amino acid or a salt thereof; the contrast medium producing contrast in the liver and abdomen that is detectable upon magnetic resonance imaging; and generating a magnetic resonance image of the liver and abdomen of said body.

12. A contrast medium composition as claimed in claim 1, further consisting essentially of a second contrast agent.

13. A composition as claimed in claim 12, wherein the second contrast agent has an opposing contrast effect to the composition consisting essentially of a physiologically acceptable manganese compound, a vitamin D, and a physiologically acceptable amino acid or a salt thereof.

14. A composition as claimed in claim 12 or claim 13, wherein the second contrast agent has a negative contrast effect.

15. A composition as claimed in claim 12 or claim 13, wherein the second contrast agent has a positive contrast effect.

16. A composition as claimed in claim 12 or claim 13, wherein the second contrast agent comprises a particulate ferromagnetic or superparamagnetic material.

17. A composition as claimed in claim 12 or claim 13, wherein the second contrast agent comprises Fe, Gd or Dy ions bound to a polymeric matrix.

18. A method according to claim 11, wherein the contrast medium further consists essentially of a second contrast agent.

19. A MRI contrast agent kit comprising in a first container a first contrast agent comprising a physiologically acceptable manganese compound, a vitamin D, a physiologically acceptable amino acid or a salt thereof, and in a second container a second contrast agent comprising a particulate ferromagnetic or superparamagnetic material.

20. A method according to claim 11, wherein the administering comprises orally administering.

* * * * *

UNITED STATES PATENT AND TRADEMARK OFFICE
CERTIFICATE OF CORRECTION

PATENT NO. : 6,015,545　　　　　　　　　　　　　　　　　　　　Page 1 of 1
DATED : January 18, 2000
INVENTOR(S) : Thomsen It is certified that error appears in the above-identified patent and that said Letters Patent is hereby corrected as shown below:

Column 1,
Line 28, ", Contrast" should read -- . Contrast --

Column 2,
Line 45, "suffient" should read -- sufficient --

Column 5,
Line 3, "species, Thus," should read -- species. Thus, --

Column 6,
Line 1, "(19.6 mg/kg)" should read -- (19.8 mg/kg) --
Line 32, "D3" should read -- $D_3$ --

Column 8, claim 14,
Line 8, delete "or claim 13" after the numeral "12"

Column 8, claim 15,
Line 11, delete "or claim 13" after the numeral "12"

Column 8, claim 16,
Line 14, delete "or claim 13" after the numeral "12"

Column 8, claim 17,
Line 17, delete "or claim 13" after the numeral "12"

Signed and Sealed this

Thirteenth Day of November, 2001

Attest:

*Nicholas P. Godici*

NICHOLAS P. GODICI
*Attesting Officer*　　*Acting Director of the United States Patent and Trademark Office*